United States Patent
Coupard et al.

(10) Patent No.: US 8,222,470 B2
(45) Date of Patent: Jul. 17, 2012

(54) PROCESS FOR OLIGOMERIZING OLEFINS USING A CATALYST BASED ON SILICA-ALUMINA

(75) Inventors: Vincent Coupard, Vaulx En Velin (FR); Alexandra Chaumonnot, Lyons (FR); Laurent Simon, Villeurbanne (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 548 days.

(21) Appl. No.: 12/360,231

(22) Filed: Jan. 27, 2009

(65) Prior Publication Data
US 2009/0192342 A1    Jul. 30, 2009

(30) Foreign Application Priority Data
Jan. 28, 2008  (FR) ..................... 08 00437

(51) Int. Cl.
*C07C 2/10* (2006.01)
*B01J 21/12* (2006.01)
(52) U.S. Cl. ........ 585/510; 502/233; 502/234; 502/235; 502/237; 502/263; 502/232; 585/520; 585/530; 585/533
(58) Field of Classification Search .................. 502/232, 502/233, 234, 235, 237, 238, 263
See application file for complete search history.

(56) References Cited

U.S. PATENT DOCUMENTS
| | | |
|---|---|---|
| 2005/0177017 A1 | 8/2005 | Euzen et al. |
| 2006/0063955 A1 | 3/2006 | Lacombe et al. |
| 2006/0079704 A1 | 4/2006 | Lacombe et al. |

FOREIGN PATENT DOCUMENTS
| | | |
|---|---|---|
| FR | 2873116 | 1/2006 |
| FR | 0800437 R | 1/2008 |

*Primary Examiner* — Elizabeth Wood
(74) *Attorney, Agent, or Firm* — Millen, White, Zelano & Branigan, P.C.

(57) ABSTRACT

A process for oligomerizing an olefinic hydrocarbon feed is described which consists of bringing said feed into contact with a catalyst comprising a silica-alumina, the silica content of said catalyst being in the range 5% to 95% by weight, said catalyst being prepared using a process comprising at least:

a) mixing at least one alumina compound which is partially soluble in an acid medium with either at least one silica compound which is completely soluble in the reaction mixture or a combination formed by at least one silica compound and at least one alumina compound, said silica and alumina compounds being completely soluble in the reaction mixture, in order to form a solid precursor of said catalyst;

b) hydrothermal treatment of the solid derived from step a) by calcining in moist air for a period in the range 4 to 7 hours.

27 Claims, No Drawings

PROCESS FOR OLIGOMERIZING OLEFINS USING A CATALYST BASED ON SILICA-ALUMINA

FIELD OF THE INVENTION

The invention relates to any process for oligomerizing olefins that can produce a fuel, for example the production of gasoline and/or kerosene from light olefinic feeds containing 2 to 8 carbon atoms, and in particular from light olefinic feeds containing a high proportion of propylene and/or butenes and/or pentenes using an oligomerization catalyst based on silica-alumina with a reduced proportion of macropores.

PRIOR ART

Processes for oligomerizing light olefins for the production of olefins with a higher molecular weight are widely used in refining and in petrochemistry, with the aim of upgrading light olefins to bases for gasoline, kerosene or gas oil type fuels, or for solvents. Such oligomerization reactions are carried out in the presence of a catalyst, usually a solid catalyst. The olefins combine into dimers, trimers, tetramers, etc, the degree of oligomerization depending on the type of catalyst used and its operating temperature, pressure and feed flow rate. The advantage of the oligomerization process over other processes which are well known in the field of refining and petrochemistry resulting in the same range of products resides in the fact that the compounds obtained contain no sulphur and contain very few aromatic compounds. The solid oligomerization catalysts often cited in the literature are catalysts of the solid phosphoric acid type (U.S. Pat. No. 2,913,506 and U.S. Pat. No. 3,661,801), silica-aluminas (for example U.S. Pat. No. 4,197,185, U.S. Pat. No. 4,544,791 and EP-0 463 673), zeolites (for example U.S. Pat. No. 4,642,404 and U.S. Pat. No. 5,284,989) and, to a lesser extent, heteropolyanions (IN 170 903).

Solid phosphoric acid type catalysts have good activity as regards oligomerization, but they are difficult to manipulate, in particular when discharging, as they tend to increase in mass in the presence of olefins. Further, they cannot be regenerated. Heteropolyanion type catalysts produce a limited degree of polymerization as they do not tolerate high temperatures well. Zeolites produce oligomers with a more limited degree of branching than the preceding catalysts because of high form selectivity in the micropores. This is favourable to gas oil production, which has to have the right cetane index, but is not favourable to the production of gasoline which has to have a high octane number. Finally, silica-alumina type catalysts cited in the literature have fairly variable porosities which result in different reactivities. As an example, EP-0 463 673 claims, for the oligomerizing propylene, the use of an amorphous silica-alumina with a $SiO_2/Al_2O_3$ molar ratio between 30 and 500, a specific surface area between 500 and 1000 $m^2/g$, a total pore volume between 0.3 and 0.6 ml/g, a mean pore diameter of at most about 1 nm, and with no pores with a diameter of more than 3 nm. U.S. Pat. No. 4,544,791 claims, for the oligomerization of $C_4$ olefins, the use of an amorphous silica-alumina with a silica content in the range 60% to 95% by weight, a specific surface area between 50 and 500 $m^2/g$, and a total pore volume between 0.4 and 0.9 ml/g, but said silica-alumina does not exhibit an alumina phase in X-ray diffraction.

Patent application US-2006/0063955 discloses a catalyst the support of which is of the non zeolitic silica-alumina type for the oligomerization of light olefins containing between 5% and 95% by weight of silica and which has a specific surface area in the range 100 to 550 $m^2/g$ and a pore volume, measured by mercury intrusion porosimetry and by nitrogen porosimetry, in the range 0.1 to 0.6 ml/g.

SUMMARY OF THE INVENTION

The present invention concerns a process for oligomerizing an olefinic hydrocarbon feed which consists of bringing said feed into contact with a catalyst comprising a silica-alumina, the silica content of said catalyst being in the range 5% to 95% by weight, said catalyst being prepared using a process comprising at least:
a) mixing at least one alumina compound which is partially soluble in an acid medium with either at least one silica compound which is completely soluble in the reaction mixture or a combination formed by at least one silica compound and at least one alumina compound, said silica and alumina compounds being completely soluble in the reaction mixture, in order to form a solid precursor of said catalyst;
b) hydrothermal treatment of the solid derived from step a) by calcining in moist air for a period in the range 4 to 7 hours.

ADVANTAGES OF THE INVENTION

Bringing at least one alumina compound which is partially soluble in an acid medium into the presence of at least one silica compound which is completely soluble in the reaction mixture or a combination formed by at least one silica compound and at least one alumina compound which are completely soluble in the reaction mixture constitutes a first step which is intended to develop specific interactions between the silica and alumina species. The hydrothermal treatment carried out in the presence of water in the liquid phase or in the gas phase for a period of at least 3 hours consecutive to the mixing envisaged in step a) of the process for preparing the catalyst constitutes a second step which can control the degree of intimacy between the alumina and silica species and thus guarantee homogeneity of the catalyst based on silica-alumina produced using the preparation process. This produces particular acidity and textural properties which result in better catalytic performances, particularly as regards selectivity during its use as a catalyst in the olefin oligomerization process.

DESCRIPTION OF THE INVENTION

Through the remainder of the text, the term "oligomerization" means any addition reaction of one olefin with a further olefin.

The present invention provides a process for oligomerizing an olefinic hydrocarbon feed, consisting of bringing said feed into contact with a catalyst comprising a silica-alumina, the silica content of said catalyst being in the range 5% to 95% by weight, said catalyst being prepared using a process comprising at least:
a) mixing at least one alumina compound which is partially soluble in an acid medium with either at least one silica compound which is completely soluble in the reaction mixture or a combination formed by at least one silica compound and at least one alumina compound, said silica and alumina compounds being completely soluble in the reaction mixture, in order to form a solid precursor of said catalyst;
b) hydrothermal treatment of the solid derived from step a) by calcining in moist air for a period in the range 4 to 7 hours.

The catalyst used in the oligomerization process of the present invention is a non zeolitic catalyst based on a silica-alumina, i.e. comprising silica and alumina. The characteristics of the silica-alumina present in the oligomerization catalyst are as follows:

- the silica content ($SiO_2$) is in the range 5% to 95% by weight, preferably in the range 10% to 80% by weight, more preferably in the range 20% to 80% by weight and still more preferably in the range 25% to 75% by weight;
- the cationic impurities content is generally less than 0.1% by weight, preferably less than 0.05% by weight and more preferably less than 0.025% by weight. The term "cationic impurities" means the total alkali compound content, in particular sodium;
- the anionic impurities content is generally less than 1% by weight, preferably less than 0.5% by weight and more preferably less than 0.1% by weight. Particular anionic impurities present in said oligomerization catalyst are halides, in particular chlorides, as well as sulphates and nitrates;
- the mean catalyst pore diameter, denoted $D_{mean}$, measured by mercury intrusion porosimetry, is in the range 20 to 140 Å, preferably in the range 40 to 120 Å and more preferably in the range 50 to 100 Å;
- the ratio between the volume V2, measured by mercury intrusion porosimetry, occupied by pores with a diameter in the range between $D_{mean}-30$ Å and $D_{mean}+30$ Å, to the total pore volume, also measured by mercury intrusion porosimetry, is more than 0.6, preferably more than 0.7 and more preferably more than 0.8;
- the volume V3 occupied by pores with diameters of more than $D_{mean}+30$ Å, measured by mercury intrusion porosimetry, is less than 0.1 ml/g, preferably less than 0.06 ml/g and more preferably less than 0.04 ml/g;
- the total pore volume, measured by mercury intrusion porosimetry, is in the range 0.6 ml/g to 0.9 ml/g, preferably in the range 0.65 to 0.9 ml/g, and more preferably in the range 0.7 to 0.9 ml/g;
- the total pore volume, measured by nitrogen adsorption isotherm, is in the range 0.6 ml/g to 0.9 ml/g, preferably in the range 0.65 to 0.9 ml/g and more preferably in the range 0.7 to 0.9 ml/g;
- the BET specific surface area is in the range 100 to 550 m2/g, preferably in the range 150 to 500 $m^2/g$, more preferably in the range 150 to 350 $m^2/g$ and still more preferably in the range 150 to 250 $m^2/g$;
- the adsorption surface area, defined using the branch of the hysteresis curve for the nitrogen adsorption isotherm for pores with a diameter in the range 3 to 200 nm, is such that the ratio between the adsorption surface area and the BET surface area is more than 0.5, preferably more than 0.65 and more preferably more than 0.8;
- the pore volume, measured by mercury intrusion porosimetry, included in pores with a diameter of more than 160 Å, is less than 0.06 ml/g, preferably less than 0.05 ml/g and more preferably less than 0.01 ml/g;
- the pore volume, measured by mercury intrusion porosimetry, included in pores with a diameter of more than 200 Å, is less than 0.06 ml/g, preferably less than 0.05 ml/g and more preferably less than 0.01 ml/g;
- the pore volume, measured by mercury intrusion porosimetry, included in pores with a diameter of more than 500 Å, is less than 0.06 ml/g, preferably less than 0.05 ml/g, more preferably less than 0.02 ml/g, and still more preferably less than 0.01 ml/g;
- the X-ray diffraction diagram of the oligomerization catalyst contains at least the principal characteristic peaks of at least one of the transition aluminas included in the group composed of alpha, rho, khi, kappa, eta, gamma, theta and delta aluminas, and preferably at least the principal characteristic peaks of at least one of the transition aluminas included in the group composed of gamma, eta, theta and delta alumina, and more preferably at least the principal characteristic peaks of gamma and eta alumina, and still more preferably the diagram contains peaks at a "d" in the range 1.39 to 1.40 Å and at a "d" in the range 1.97 Å to 2.00 Å.

The settled packing density of the oligomerization catalyst is more than 0.40 $g/cm^3$, preferably more than 0.45 $g/cm^3$, and more preferably more than 0.50 $g/cm^3$.

The silica-alumina present in the catalyst used in the process of the invention is preferably a silica-alumina which is homogeneous on the micrometric scale and in which the cationic impurities content, especially the cation $Na^+$, is less than 0.1% by weight, preferably less than 0.05% by weight and more preferably less than 0.025% by weight and the anionic impurities content, for example $SO_4^{2-}$ or $Cl^-$, is less than 1% by weight, preferably less than 0.5% by weight and more preferably less than 0.1% by weight.

Thus, any silica-alumina synthesis process known to the skilled person leading to a silica-alumina having the acidity properties and textural properties defined hereinabove, in particular characterized by a homogeneity of the silica and alumina species on the micrometric scale and even on the nanometric scale and in which the cationic impurities content (for example $Na^+$) can be reduced to less than 0.1% by weight, preferably to less than 0.05% by weight and more preferably to less than 0.025% by weight and in which the anionic impurities content, for example $SO_4^{2-}$ or $Cl^-$, may be brought to less than 1% by weight, preferably to less than 0.5% by weight and still more preferably to less than 0.1% by weight, is suitable for the preparation of the oligomerization catalysts used in the process of the invention.

In one embodiment of the oligomerization catalyst used in the process of the invention, said catalyst contains at least two silico-alumina zones, said zones having Si/Al molar ratios which are lower or higher than the overall Si/Al molar ratio determined by X-ray fluorescence. Thus, a catalyst having an overall Si/Al molar ratio of 0.5 comprises, for example, two silica-alumina zones, one of the zones having a Si/Al molar ratio determined by TEM of less than 0.5 and the other zone having a Si/Al molar ratio determined by TEM of between 0.5 and 2.5.

In one embodiment of the oligomerization catalyst used in the process of the invention, the catalyst contains a single silica-alumina zone, said zone having a Si/Al molar ratio equal to the overall Si/Al molar ratio, determined by X-ray fluorescence, of less than 6.

In accordance with the invention and in preferred embodiment of the oligomerization catalyst used in the process of the invention, said catalyst is wholly constituted by said silica-alumina; it is free from any other element.

Solid $^{27}Al$ MAS NMR spectra of the oligomerization catalyst based on silica-alumina used in the process of the invention exhibit two distinct peak masses. A first type of aluminium with a maximum resonating at about 10 ppm extends between −100 and 20 ppm. The position of the maximum suggested that these species were essentially of the $Al_{VI}$ type (octahedral). A second minor type of aluminium with a maximum resonating at about 60 ppm extends between 20 and 110 ppm. This can be differentiated into at least two species. The predominant species here corresponds to $Al_{IV}$ atoms (tetrahedral). For the oligomerization catalyst based on silica-alumina used in the process of the present invention, advantageously, the proportion of octahedral $Al_{VI}$ is more than 50 molar %, preferably more than 60 molar %, and more preferably more than 70 molar %.

The acidity of the oligomerization catalyst used in the process of the invention is advantageously measured by IR monitoring of the thermodesorption of pyridine. In general, the ratio B/L, as described below, of the oligomerization catalyst used in the process of the invention is in the range 0.05 to 6, preferably in the range 0.5 to 2.

The oligomerization catalyst used in the process of the invention may optionally contain at least one metallic element selected from metals from groups IVB, VB, VIB and VIII. Group IVB metals include titanium, zirconium and/or hafnium which may be present in the catalyst. Group VB metals include vanadium, niobium and/or tantalum which may be present in the catalyst. Group VIB metals include chromium, molybdenum and/or tungsten which may be present in the catalyst. Of the metals from group VIII, metals from the first line of metals from group VIII, namely iron, cobalt and nickel, are preferred. The amount of these metals may be up to 10% of the final catalyst weight. The catalyst may optionally also contain silicon as the doping element deposited on the silica-alumina.

The Applicant has discovered that the catalyst based on silica-alumina obtained from a mixture of at least one alumina compound which is partially soluble in an acid medium with either at least one silica compound which is completely soluble in the reaction mixture or a combination formed by at least one silica compound and at least one alumina compound, said silica and alumina compounds being completely soluble in the reaction mixture, followed by homogenization on the micrometric scale, or even on the nanometric scale of said mixture via a hydrothermal treatment lasting at least 3 hours, can produce a catalyst which is particularly selective as regards carrying out the oligomerization process of the invention. Bringing at least one alumina compound which is partially soluble in an acid medium into the presence of at least one silica compound which is completely soluble in the reaction mixture or a combination formed by at least one silica compound and at least one alumina compound which are completely soluble in the reaction mixture corresponds to bringing alumina species and silica species with a specific size and chemical reactivity into contact in said mixture envisaged in step a) of the process for preparation of the catalyst, thereby resulting in controlled interactions between said species which are partly at the origin of the homogeneity of the silica-alumina present in the catalyst used to carry out the oligomerization process of the invention. Depending on the chemical nature of the alumina and silica compounds used to prepare the catalyst, controlling the degree of interactivity between the silica and alumina species may be carried out at any step in the preparation process preceding the hydrothermal treatment step. By way of non-limiting example, mixing a partially soluble alumina compound of the hydrated aluminium type, $Al_2O_3,nH_2O$ (boehmite) with a completely soluble silica compound of the decationized orthosilicic acid type may be carried out in an aqueous medium under the influence of various controlled operating parameters for the synthesis (pH, temperature, etc), or a partially soluble alumina compound of the aluminium hydrate type $Al_2O_3,nH_2O$ (boehmite) may be mixed with a completely soluble commercial silica (Ludox®) colloidal solution during the shaping step consecutive to the mechanical work generated during this shaping process. To finish, the hydrothermal treatment carried out in the presence of water—in the vapour phase or in the liquid phase—consecutive to the mixing envisaged in step a) of the process for preparing the oligomerization catalyst can finally provide the degree of homogeneity on the micrometric or even the nanometric scale between the alumina and silica species necessary to the development of the acidity and textural properties of the catalyst used in the olefin oligomerization process of the invention.

In accordance with a first implementation of step a) of the process for preparing the oligomerization catalyst used in the process of the invention, at least one alumina compound which is partially soluble in an acid medium is mixed with at least one silica compound which is completely soluble in the reaction mixture. The sources of the completely soluble silica compound brought into the presence with at least one alumina compound which is partially soluble in an acid medium are advantageously selected from the group formed by silicic acid, colloidal solutions of silicic acid, hydrosoluble alkaline silicates and cationic silicon salts, for example hydrated sodium metasilicate, Ludox® in the ammonia form or in the alkaline form and quaternary ammonium silicates. The colloidal solutions of silicic acid may be prepared using one of the methods known to the skilled person. Preferably, the source of the completely soluble silicic compound which is used is prepared from a hydrosoluble alkaline silicate by ion exchange on a resin.

In accordance with a second implementation of step a) of the process for preparation of an oligomerization catalyst used in the process of the invention, at least one alumina compound which is partially soluble in an acid medium is mixed with a combination formed by at least one silica compound and at least one alumina compound, said silica and alumina compounds being completely soluble in the reaction mixture. Of the sources of said combination, completely soluble hydrated silica-aluminas are advantageously used. They are preferably prepared by true co-precipitation under controlled stationary operating conditions (pH, concentration, temperature, mean residence time) or by reaction of a basic solution containing silicon, for example in the form of sodium silicate, optionally aluminium, for example in the form of sodium aluminate, with an acid solution containing at least one aluminium salt, for example aluminium sulphate. At least one carbonate or $CO_2$ may optionally be added to the reaction medium regardless of the preparation mode.

The term "true co-precipitation" means a process in which at least one alumina compound and at least one silica compound which are completely soluble in a basic medium or in an acid medium as described above are brought into contact, simultaneously or sequentially, in the presence of at least one precipitating and/or co-precipitating compound to obtain a mixed phase which is essentially constituted by hydrated silica-alumina which is optionally homogenized by intense agitation, shear, colloidal milling or by a combination of these individual operations. As an example, these hydrated silica-aluminas may have been prepared as described in the following American patents: U.S. Pat. No. 2,908,635; U.S. Pat. No. 3,423,332; U.S. Pat. No. 3,433,747; U.S. Pat. No. 3,451,947; U.S. Pat. No. 3,629,152 and U.S. Pat. No. 3,650,988.

In accordance with step a) of the process for preparing the oligomerization catalyst used in the oligomerization process of the invention, at least one silica compound which is completely soluble in the reaction mixture or a combination formed by at least one silica compound and at least one alumina compound, said silica and alumina compounds being completely soluble in the reaction mixture, is mixed with at least one alumina compound which is partially soluble in an acid medium. The property of total dissolution in the reaction mixture of said silica compound or said silica and alumina compounds forming said combination was determined approximately using the following method. A fixed quantity (15 g) of the silica compound or said combination, preferably hydrated, is introduced into an aqueous medium at a fixed pH. Preferably, the concentration of solid, namely that of the silica compound or the silica and alumina compounds, with respect to a liter of suspension, is 0.2 moles per liter. The pH of the solution is at least 12 and may be obtained using an alkaline source. Preferably, NaOH is advantageously used. The mixture is then mechanically stirred using a deflocculating turbine agitator for 30 minutes at 800 rpm. Once agitation is complete, the mixture is centrifuged for 10 minutes at 3000 rpm. The cake is separated from the supernatant liquid: the solution is filtered through a filter with a pore size of 4 and a diameter of 19 cm. Drying and calcining of the 2 fractions, namely that of the cake and that of the liquid supernatant, is carried out at 1000° C. A ratio R is determined by dividing the solid equivalent mass of the cake by the mass of the solid present in the supernatant. The term "completely soluble" is applied to a ratio R of at least 0.9.

In order to carry out step a) of the process for preparing the oligomerization catalyst used in the process of the invention, an alumina compound which is partially soluble in an acid medium is advantageously selected from the group of alumina compounds with general formula $Al_2O_3$,n $H_2O$ ($n \leq 5$) and with a specific surface area in the range 150 to 600 $m^2/g$. In particular, hydrated alumina compounds may be used, such as: hydrargillite, gibbsite, bayerite, boehmite, pseudo-boehmite and amorphous or essentially amorphous alumina gels. It is also possible to use dehydrated forms of said compounds which are constituted by transition aluminas and which comprise at least one of the phases in the following group: alpha, rho, khi, eta, gamma, kappa, theta, and delta, which essentially differ from each other in the organization of their crystalline structure.

The term "partially soluble in an acid medium" means that contact of said alumina compound with an acidic solution, for example nitric acid or sulphuric acid, causes its partial dissolution before either at least one silica compound which is completely soluble in the reaction mixture or a combination formed by at least one silica compound and at least one alumina compound is added, said silica and alumina compounds being completely soluble in the reaction mixture.

This partial dissolution property is an important property for the preparation of the catalyst used in the process of the invention. It is applicable to hydrated alumina powders, to spray dried hydrated alumina powders, to dispersions or suspensions of hydrated alumina or to any combination thereof, prior to any addition of a compound containing all or part of the silicon.

Said partial dissolution of said alumina compound is approximated using the following method. A precise quantity of the powdered alumina compound or suspended alumina compound is introduced into an aqueous medium at a predetermined pH. The mixture is then mechanically stirred. Once agitation is complete, the mixture is left without agitation for 24 hours. Preferably, the concentration of solid $Al_2O_3$ with respect to one liter of suspension is 0.5 moles per liter. The pH of the suspension solution is 2 and is obtained either by using $HNO_3$ or HCl or $HClO_4$. Preferably, $HNO_3$ is used. The aluminium distribution is such that a first portion of the aluminium is present in a sedimented fraction and a second portion of the aluminium is present in a dissolved fraction. The distribution of the aluminium in each of these two fractions is followed by assaying the aluminium by UV absorption. The dissolved fraction, also termed the supernatant, is ultrafiltered (polyether-sulphone membrane, Millipore NMWL 30000) and digested in concentrated acid. The quantity of aluminium in said dissolved fraction (supernatant) corresponds to the non-sedimented alumina compound and to the dissolved aluminium, and the ultrafiltered fraction corresponds to the dissolved aluminium alone. The quantity of sedimented particles is deduced from the theoretical concentration of aluminium in the dispersion (assuming that all of the solid which has been introduced is in suspension) and the quantities of non-sedimented aluminium in suspension and dissolved aluminium in solution. The presence of sedimented particles characterizes the partial dissolution property.

The alumina precursors used for their property of partial dissolution in the preparation of the catalyst employed in the process of the present invention are thus distinguished from those used in the case of true co-precipitation, which are entirely soluble in an acid medium, such as cationic alumina salts, for example aluminium nitrate, or in a basic medium. The methods using said alumina precursors used for their property of partial dissolution are distinguished from the true co-precipitations since one of the elements, in this case the aluminium compound, is partially soluble.

More preferably, the aluminium hydrate, $Al_2O_3$,$nH_2O$, used is boehmite, pseudo-boehmite and amorphous or essentially amorphous alumina gels. A mixture of said products in any combination may also be used. Boehmite is generally described as an aluminium monohydrate with formula $Al_2O_3$, $nH_2O$ which encompasses a wide range of materials with varying degrees of hydration and organization the distinctions between which may be blurred: the most hydrated gelatinous boehmite, in which n may be greater than 2, pseudo-boehmite or micro-crystalline boehmite in which n is in the range 1 to 2, then crystalline boehmite, and finally boehmite properly crystallized into large crystals with n close to 1. The morphology of aluminium monohydrate may vary widely between the two limiting forms, acicular and prismatic. A whole series of various forms may be used between these two forms: chains, boats, interlaced plates. Many patents relate to the preparation and/or shaping of solids based on transition alumina derived from aluminium monohydrate: U.S. Pat. No. 3,520,654, U.S. Pat. No. 3,630,670, U.S. Pat. No. 3,864,461, U.S. Pat. No. 4,154,812, U.S. Pat. No. 4,313, 923, DE 3 243 193 and U.S. Pat. No. 4,371,513.

Relatively pure aluminium hydrates may be used in the form of powders, which may be amorphous or crystalline, or crystalline powder containing an amorphous portion. The aluminium hydrate may also be introduced in the form of aqueous suspensions or dispersions. The aqueous aluminium hydrate suspensions or dispersions employed to prepare the catalyst used in the process of the invention may be capable of being gelled or coagulated. Acidic aqueous dispersions or suspensions may also be obtained, as is well known to the skilled person, by peptization of aluminium hydrates in water or in an aqueous solution of hydrates of aluminium.

The aluminium hydrate dispersion may be produced by any process which is known to the skilled person: in a "batch" reactor, a continuous mixer, a grinder, or a colloidal mill. Such a mixture may also be produced in a plug flow reactor and in particular in a static mixer. "Lightnin" reactors can be cited.

Further, the source of alumina compound which is partially soluble in an acid medium may also be an alumina which has already undergone a treatment which can improve its degree of dispersion. As an example, it is possible to improve the dispersion of the alumina source by a preliminary mechanical homogenization treatment.

The aqueous dispersions or suspensions of alumina which may be used are fine or ultrafine aqueous suspensions or dispersions of boehmites which are composed of particles with colloidal dimensions. The fine or ultrafine boehmites used in accordance with the present invention may in particular have been obtained in accordance with patents FR-1 261 182 and FR-1 381 282 or European patent application EP-0 015 196. It is also possible to use aqueous suspensions or dispersions obtained from pseudo boehmite, amorphous alumina gels, aluminium hydroxide gels or ultrafine hydrargillite gels.

Aluminium monohydrate may be purchased from a variety of commercial sources of alumina such as PURAL®, CATAPAL®, DISPERAL®, DISPAL® sold by SASOL, or HIQ® sold by ALCOA, or using methods which are known to the skilled person: by partial dehydration of aluminium trihydrate using conventional methods, or by precipitation. When the aluminas are in the form of a gel, they are peptized by water or an aqueous acidic solution. For precipitation, the source of the acid may, for example, be at least one of the following compounds: aluminium chloride, aluminium sulphate or aluminium nitrate. The source of basic aluminium may be selected from basic aluminium salts such as sodium aluminate or potassium aluminate. Examples of precipitating agents which may be used are sodium hydroxide, sodium carbonate, potassium hydroxide and ammonia. The precipitating agents are selected so that the alumina source of the present invention and these agents are precipitated together. Depending on the acidic or basic nature of the starting aluminium-based compound, the aluminium hydrate is precipitated using a base or an acid selected, for example, from hydrochloric acid, sulphuric acid, sodium hydroxide or a basic or acidic aluminium compound such as those cited above. The two reagents may be aluminium sulphate and sodium aluminate. As an example, the preparation of aluminium alpha-monohydrate using aluminium sulphate and sodium aluminate is described in U.S. Pat. No. 4,154,812. Pseudo-boehmite may be prepared using the process described in U.S. Pat. No. 3,630,670 by reacting an alkaline aluminate solution with a mineral acid solution. It may also have been prepared as described in FR-1 357 830. Amorphous alumina gels may be prepared using the processes described in the article "Alcoa Paper 1972, 19, 9, and in particular by reacting an aluminate or an aluminium salt, or by hydrolysis of aluminium alcoholates or by hydrolysis of basic aluminium salts. The aluminium hydroxide gels may be those prepared using the processes described in U.S. Pat. No. 3,268,295 and U.S. Pat. No. 3,245,919 or in patent application WO-00/01617, by mixing an acidic source of aluminium and a base or a basic source of aluminium and an acid to precipitate an alumina monohydrate, said mixture being produced without back-mixing. Ultra-fine hydrargillite may in particular be prepared using the process described in U.S. Pat. No. 1,371,808, by alumina gels at a temperature in the range between ambient temperature and 60° C. into a cake.

It is also possible to use, as sources of the alumina compound which is partially soluble in an acid medium, aqueous suspensions or dispersions of ultrapure boehmite or pseudo-boehmite prepared using a process in which an alkaline aluminate is reacted with carbonic anhydride to form a precipitate of amorphous aluminium hydroxycarbonate. The precipitate is obtained by filtering then washing. Such a process has been described in U.S. Pat. No. 3,268,295. Next, 1) in a first step, the washed amorphous aluminium hydroxycarbonate precipitate is mixed with a solution of an acid, a base or a salt or a mixture thereof (this mixture is made by pouring the solution onto the hydroxycarbonate, the pH of the medium so constituted being less than 11); 2) in a second step, the reaction mixture formed is heated to a temperature of less than 90° C. for a period of at least 5 minutes; and 3) in a third step, the medium resulting from the second step is heated to a temperature in the range 90° C. to 250° C. The boehmite and pseudo-boehmite dispersions or suspensions obtained using this process have an alkali content of less than 0.005% expressed in the form of the ratio of the alkali metal oxide/$Al_2O_3$.

For a catalyst based on very pure silica-alumina, ultrapure suspensions or dispersions of boehmites or pseudo-boehmites are used, obtained using the process described above, or aluminium hydroxide gels which have been prepared by hydrolysis of aluminium alcoholates preferably using a process of the type described in U.S. Pat. No. 2,892,858.

We shall now summarize the production process which produces such boehmite type aluminium hydroxide gels, obtained as a by-product in the production of alcohol by hydrolysis of an aluminium alcoholate or alkoxide (Ziegler synthesis). Ziegler alcohol synthesis reactions have been described in particular in U.S. Pat. No. 2,892,858. In that process, triethylaluminium is initially prepared from aluminium, hydrogen and ethylene, the reaction being carried out in two steps with a partial recycle of the triethylaluminium. Ethylene is added in the polymerization step and the product obtained is then oxidized to aluminium alcoholate, the alcohols being obtained by hydrolysis. The aluminium hydroxide gels may also be those which are prepared in accordance with the processes described in U.S. Pat. No. 4,676,928 and U.S. Pat. No. 6,030,599. The hydrated alumina obtained as a by-product of the Ziegler reaction is that described in a bulletin from CONOCO dated 19 Jan. 1971.

The dimensions of the alumina particles constituting the source of alumina may vary widely. They are generally in the range 1 to 100 microns.

Methods for Preparing the Oligomerization Catalyst

The catalyst used in the oligomerization process of the invention is prepared using a synthesis process comprising at least the following two steps:

a) mixing at least one alumina compound which is partially soluble in an acid medium with either at least one silica compound which is completely soluble in the reaction mixture or a combination formed by at least one silica compound and at least one alumina compound, said silica and alumina compounds being completely soluble in the reaction mixture, in order to form a solid precursor of said catalyst;

b) hydrothermal treatment of the solid from step a) for a period of at least 3 hours.

The mixture mentioned in step a) of the process for preparation of the catalyst used in the oligomerization process of the invention may, for example, be produced by one of the methods described below.

One example of a method for preparing said mixture envisaged in step a) of the process for preparation of the catalyst used in the oligomerization process of the invention consists of preparing a solution of orthosilicic acid ($H_2SiO_4$, $H_2O$) decationized by ion exchange from a hydrosoluble alkaline silicate then adding it to a mixture constituted by a cationic aluminium salt in solution (for example the nitrate), and ammonia under controlled operating conditions; or adding it to the cationic aluminium salt in solution and then co-precipitating the solution obtained with ammonia under controlled operating conditions, the two possible options resulting in a homogeneous product, namely a silica-alumina hydrogel. This silica-alumina hydrogel, a combination of an alumina compound and a completely soluble silica compound, is mixed with an aluminium hydrate powder or suspension, an alumina compound which is partially soluble in an acid medium. After filtering, washing and drying followed by optional shaping, a solid precursor of the oligomerization catalyst is obtained. It is ready to undergo the hydrothermal treatment envisaged in step b) of the process for preparing the oligomerization catalyst.

Another example of a method for preparing said mixture envisaged in step a) of the process for preparation of a catalyst used in the oligomerization process of the invention consists of precipitating the alumina hydrate as described above, filtering and washing it, then mixing it with aqueous orthosilicic acid which is used as the completely soluble silica compound to obtain a suspension, which is intimately mechanically homogenized by strong agitation and shearing. An Ultraturrax® turbine or a Staro® turbine may be used, or a colloidal mill, for example a Staro® colloidal mill. The homogeneous suspension is then dried by spraying, and optionally calcined between 500° C. and 1200° C. for at least 3 hours before optional shaping. A solid precursor of the catalyst is obtained and is ready to undergo the hydrothermal treatment in the presence of steam envisaged in step b) of the process for preparing the oligomerization catalyst.

A further example of a method for producing said mixture envisaged in step a) of the process for preparation of the catalyst used in the oligomerization process of the invention consists of preparing, as above, a solution of decationized orthosilicic acid (completely soluble silica compound), then simultaneously or consecutively adding it to an alumina compound which is partially soluble in an acid medium, for example an aluminium hydrate in powdered form or in acidic suspension. To increase the pore diameter of the final silica-alumina catalyst, at least one basic compound may optionally be added to the reaction medium. After intense mechanical homogenization of the suspension by agitation, optional adjustment of the dry matter content by filtering and optional re-homogenization, the product is dried with possible simultaneous or consecutive shaping, then optionally calcined, preferably in air, in a rotary oven, at a high temperature and for a period which is generally at least 2 hours before undergoing step b) of the process for preparing the oligomerization catalyst.

A further example of a method for preparing said mixture envisaged in step a) of the process for preparation of the catalyst used in the oligomerization process of the invention consists of preparing an aqueous suspension or dispersion of alumina, for example an aluminium monohydrate (alumina compound which is partially soluble in an acid medium), then adding it simultaneously or consecutively to a completely soluble silica compound, for example a sodium silicate. To increase the pore diameter of the final silica-alumina catalyst, at least one basic compound may optionally be added to the reaction medium. Next, filtering and at least one wash are carried out, optionally by washing at least once with an ammoniacal solution to extract the residual sodium by ion exchange. After drying and optional shaping then calcining as before, a solid catalyst precursor is obtained. It is ready to undergo the hydrothermal treatment envisaged in step b) of the process for preparing the oligomerization catalyst.

To increase the diameter of the mesopores of the final silica-alumina catalyst, it may be particularly advantageous, as disclosed in U.S. Pat. No. 4,066,574, to prepare said mixture envisaged in step a) of the process for preparing the oligomerization catalyst by producing an aqueous suspension or dispersion of alumina catalyst, for example an aluminium monohydrate (alumina compound which is partially soluble in an acid medium), then to neutralize it with a basic solution, for example ammonia, and finally to simultaneously or consecutively add it to a completely soluble silica compound, for example a decationized orthosilicic acid solution. After intense mechanical homogenization of the suspension by intense agitation, optional adjustment of the dry matter content by filtering and re-homogenization, the product is dried with optional simultaneous or consecutive shaping, then optionally calcined as above. A solid precursor of the catalyst is thus obtained. It is ready to undergo the hydrothermal treatment envisaged in step b) of the process for preparing the oligomerization catalyst.

In the description below of the methods cited above, a first "homogenization" of said mixture is often carried out using mechanical treatments such as, for example, when taking a product containing a solid fraction up into solution, such as a suspension, a powder, a filtered precipitate, followed by dispersing it with intense agitation. Mechanical homogenization of a dispersion is a process which is well known to the skilled person. Said homogenization may be carried out using any mechanical process which is known to the skilled person, for example in a batch reactor, a continuous mixer or a mill. Said mixing may be carried out in a plug reactor, in particular in a static reactor. "Lightnin" reactors may be cited. An Ultraturrax® turbine or a Staro® turbine may be used, or a colloidal mill, for example a Staro colloidal mill. Commercially available IKA® colloidal mills may also be used.

In the methods cited above, it may optionally be desirable to add, during any step of the preparation, a small proportion of at least one stabilizing element selected from the group formed by zirconium and titanium. The stabilizing element is preferably added in the form of a soluble salt.

In accordance with step b) of the process for preparation of the catalyst used in the oligomerization process of the invention, the hydrothermal treatment, carried out for a period in the range 4 to 7 hours, of the solid from said step a) described above can ensure homogeneity of the solid support resulting from step a) of the process for preparing the oligomerization catalyst. Said hydrothermal treatment is carried out by calcining in moist air. Said hydrothermal treatment consists of bringing the solid from said step a) described above into contact with water, in the vapour or liquid phase, at any production stage. Without wishing to restrict the scope of the invention, such a treatment has the effect of rendering the silica component mobile.

Said hydrothermal treatment by calcining in moist air is carried out in a furnace in the presence of steam. The temperature applied during calcining in moist air is advantageously in the range 600° C. and 1100° C. and preferably in the range 650° C. to 800° C. The period of said hydrothermal treatment is in the range 4 to 7 hours. Said calcining in moist air is carried out in the presence of a quantity of steam of more than 20 g of water per kg of dry air, preferably more than 40 g of water per kg of dry air, more preferably more than 100 g of water per kg of dry air and still more preferably more than 300 g of water per kg of dry air.

Shaping Catalyst

The oligomerization catalyst used in the process of the invention is in the form of spheres, pellets or extrudates, preferably extrudates. Highly advantageously, said oligomerization catalyst is in the form of extrudates with a diameter in the range 0.5 to 5 mm, more particularly in the range 0.7 to 2.5 mm. The shapes are cylindrical (they may or may not be hollow), twisted cylinders, multilobes (2, 3, 4 or 5 lobes, for example), or rings. The cylindrical and multilobed shape is preferably used, but any other form may be used.

The oligomerization catalyst used in the process of the invention is obtained by shaping the silica-alumina using any technique which is known to the skilled person. Shaping may, for example, be carried out by extrusion, pelletization, drying, spray drying, by the oil drop coagulation method, by rotating plate granulation or by any other method which is known to the skilled person.

Shaping may also be carried out in the presence of various constituents of the catalyst and extrusion of the mineral paste obtained, by pelletization, by shaping into beads on a rotating bowl granulator or drum, by oil drop coagulation, oil-up coagulation or by any other known method for agglomeration of a powder containing alumina and silica and optional other ingredients selected from those mentioned above.

More precisely, when the catalyst is in the form of extrudates, water may be added or withdrawn to adjust the viscosity of the paste to be extruded. This step may be carried out at any stage in the mixing step. To adjust the amount of solid material in the paste to be extruded in order to render it capable of being extruded, a compound which is primarily solid, preferably an oxide or a hydrate, may also be added. Preferably, a hydrate is used, and more preferably a hydrate of aluminium. The loss on ignition of this hydrate is more than 15%.

The quantity of acid added on mixing before shaping is less than 30%, preferably in the range 0.5% to 20% by weight of the anhydrous mass of silica and alumina engaged in the synthesis. Extrusion may be carried out using any conventional tool which is commercially available. After mixing, the paste is extruded through a die, for example using a piston or a single or double extrusion screw. This extrusion step may be carried out using any method which is known to the skilled person. The extrudates of the oligomerization catalyst used in the process of the invention generally have a crush strength of at least 70 N/cm and preferably 100 N/cm or more.

Further, said oligomerization catalyst used in the process of the present invention may have been treated, as is well known to the skilled person, with additives to facilitate shaping and/or to improve the final mechanical properties of said catalyst based on silica-alumina. Examples of additives which may be cited are cellulose, carboxymethyl cellulose, carboxyethyl cellulose, xanthan gums, surfactants, flocculating agents such as polyacrylamides, carbon black, starches, stearic acid, polyacrylic alcohol, polyvinyl alcohol, biopolymers, glucose, polyethylene glycols, etc.

Partial adjustment of the characteristic porosity of the catalysts of the invention is carried out during this step for shaping the catalyst particles.

Drying and Calcining Catalyst

To prepare the oligomerization catalyst, one or more steps for drying and one or more calcining steps are carried out when carrying out the process for preparing the oligomerization catalyst.

Drying is carried out using any technique which is known to the skilled person. As mentioned above, it is advantageous to carry out at least one calcining step on the solid based on silica-alumina from step a) of the process for preparing the oligomerization catalyst, before carrying out step b) of this same preparation process or to carry out said calcining step at any intermediate step to produce the solid based on silica-alumina of step a) of the process for preparing the catalyst described above in the present description. It is generally preferable to calcine in the presence of molecular oxygen, for example by carrying out a flush of air, at a temperature of 1100° C. or less. This treatment may, for example, be carried out in a flushed bed, trickle bed or in a static atmosphere. As an example, the furnace used may be a rotary furnace or a vertical furnace with radial flow layers. The calcining conditions—temperature and duration—principally depend on the maximum catalyst service temperature; the preferred calcining conditions are more than one hour at 200° C. and less than one hour at 1100° C. Calcining may be carried out in the presence of steam. Final calcining may optionally be carried out in the presence of an acidic or basic vapour. As an example, calcining may be carried out in a partial pressure of ammonia.

In accordance with a highly preferred process for preparing the oligomerization catalyst as described above, initially the mixture envisaged in said step a) is used to obtain the solid constituted by a silica-alumina precursor of the oligomerization catalyst. Next, said solid is shaped into extrudates as described above. Said extrudates are then dried and calcined. Finally, they undergo a hydrothermal treatment in accordance with step b) of the process for preparing the oligomerization catalyst; preferably, said treatment is calcining in moist air.

Description of the Oligomerization Process

The process of the invention is a process for oligomerizing olefins to produce a fuel, for example the production of gasoline and/or kerosene from light olefinic feeds containing between 2 and 8 carbon atoms, in particular from light olefinic feeds containing a high proportion of propylene and/or butenes and/or pentenes using an oligomerization catalyst based on silica-alumina with a reduced number of macropores. Preferably, said catalyst is constituted solely by silica-alumina.

Feeds

The olefins present in the olefinic hydrocarbon feed may, for example, derive from a catalytic cracking unit and/or from a steam cracking unit and/or from a paraffin dehydrogenation unit and/or from a unit for the polymerizing dehydration of methanol to water and light olefins and/or from any other source leading to the production of light olefins.

The olefinic hydrocarbon feed sent to the oligomerization reactor used to carry out the process of the invention, containing the catalyst prepared using the process described above, is preferably free of impurities such as water, sulphur-containing derivatives, basic nitrogen-containing derivatives, before being introduced into the oligomerization reactor.

The olefinic hydrocarbon feed may be an olefinic C4 cut, which normally comprises more than 90% by weight of isobutane, n-butane, 1-butene, 2-butenes, isobutene and possibly a small quantity of butadiene. The butadiene is generally eliminated upstream of the oligomerization step by a selective hydrogenation process.

The olefinic hydrocarbon feed may also be an olefinic C3-C4 cut. The composition of the C3-C4 olefinic cut is highly variable, depending on its provenance. It may comprise between about 20% and 50% by weight of propylene and propane, between about 50% and 80% by weight of isobutane, n-butane, 1-butene, 2-butenes, isobutene, and possibly a small quantity of butadiene. The butadiene is generally eliminated upstream of the oligomerization step by a selective hydrogenation process.

The olefinic hydrocarbon feed may also be an olefinic C3 cut. It normally comprises at least 90% by weight of propylene and propane.

The olefinic hydrocarbon feed may also be an olefinic C5 cut. The composition of the olefinic C5 cut varies widely depending on its provenance. It advantageously comprises 30% to 80% by weight of C5 olefins, between 1% and 20% by weight of C6 olefins and between 1% and 10% by weight of C4 olefins.

In accordance with the invention, the exothermicity of the oligomerization reaction may be managed by recycling at least a portion of the unconverted effluent, which in particular contains paraffins which have not been transformed during the reaction, to the oligomerization reactor, and/or the feed may be diluted by adding paraffins from another source, said paraffins being of the same molecular weight and/or heavier than the olefinic feed, said paraffins being aliphatic or cyclic.

In all of the processes resulting in the formation of gasoline and/or kerosene, and/or more generally an olefinic cut with a boiling point commencing at a temperature of more than 150° C., the olefinic cuts obtained at the end of the process may also be partially or completely hydrogenated.

Implementations of the Oligomerization Process of the Invention

First Implementation: Selective Oligomerization

In said first implementation, an olefinic C4 cut is brought into contact with the catalyst comprising a silica-alumina prepared using the process described in the present description in a manner that limits the overall conversion of n-butenes to less than 10%, preferably to less than 5%, while more than 90% by weight of the quantity of isobutene is converted, preferably more than 95%. The isobutene is more than 90% by weight converted into dimers and trimers. Subsequently, the oligomerization effluent undergoes distillation such that the recovered fractions (light effluent) contain more than 90% by weight of butane, isobutane and butenes which have not reacted during the oligomerization, at least a portion of said fraction then supplying an alkylation unit or a hydration unit, for example, while the other fraction constituted by the oligomers obtained is used as gasoline stock, optionally after partial or complete hydrogenation.

The implementation of the oligomerization process described above corresponds to the implementation termed "selective oligomerization" in which primarily isobutene is converted.

In accordance with said first implementation of the oligomerization process of the invention, the oligomerization reaction is carried out at a temperature in the range 30° C. to 300° C., at a pressure in the range 0.1 to 20 MPa and with a volume of olefinic hydrocarbon feed per volume of catalyst per hour in the range 0.05 to 5 $h^{-1}$. Preferably, the temperature is between 40° C. and 160° C., and the pressure is between 2 and 7 MPa, to ensure that the reaction is carried out in the liquid phase or at least in a homogeneous phase (i.e. entirely in the liquid phase or entirely in the gas phase), and the volume of olefinic hydrocarbon feed sent per volume of catalyst per hour is preferably in the range 0.1 to 2.5 $h^{-1}$.

The oligomerization reactor technology may be that of a fixed bed, fluidized bed or moving bed reactor. Preferably, it is a fixed bed reactor.

Preferably, the oligomers obtained are re-injected into a supplemental oligomerization reactor containing, for example, the oligomerization catalyst comprising a silica-alumina as described above, to increase the chain length of the oligomers and thus obtain the kerosene cut, or more generally an olefinic cut with an initial boiling point at a temperature of more than 150° C.

Advantageously, the light oligomerization effluent, i.e. the C4 cut, may be introduced into a hydroisomerization reactor to hydroisomerize a portion of the 1-butene which is not converted into 2-butene, to approach thermodynamic equilibrium. The other constituents of the effluent are thus not significantly converted during the hydroisomerization step. The conversion of 1-butene to 2-butene is very useful if the C4 fraction obtained from the hydroisomerization reactor outlet may then be introduced into a reactor for aliphatic alkylation over hydrofluoric acid, the products obtained by alkylation of 2-butene with isobutane having a better octane number than the alkylate obtained from 1-butene.

Given the highly exothermic nature of the oligomerization reaction, the quantity of isobutene in the hydrocarbon feed supplying the oligomerization reactor is preferably less than 35% by weight, more preferably less than 15% by weight, said quantity optionally having been obtained by diluting the feed, for example with butane or isobutane or raffinate from the oligomerization unit.

Second Implementation

In said second implementation, a C4 olefinic cut or C3-C4 olefinic cut is brought into contact with the oligomerization catalyst described in the present description such that a portion of the butenes contained in the hydrocarbon feed are converted into dimers or trimers, then used as gasoline stock. In this second implementation of the process of the invention, less than 80% by weight of the butenes are converted and at least 80% by weight, preferably at least 90% by weight, of the isobutene is converted. This process can maximize the quantity of gasoline while minimizing the quantity of kerosene formed.

In the oligomerization reactor used to carry out said second implementation, the temperature is between 40° C. and 250° C., preferably between 50° C. and 200° C., and the pressure is between 0.1 and 10 MPa, preferably between 0.1 and 6 MPa, and the quantity of hydrocarbon feed sent per volume of catalyst per hour is in the range 0.05 to 5 $h^{-1}$, preferably in the range 0.1 to 2.5 $h^{-1}$. The reactor technology may be that of a fixed bed, fluidized bed or moving bed reactor. Preferably, a fixed bed reactor is used.

In a variation of this second implementation of the process of the invention, the feed is an olefinic feed from which the isobutene has been partially or completely eliminated, for example using an etherification unit upstream of the oligomerization unit, selectively reacting the isobutene with an alcohol, for example methanol or ethanol, without converting n-butene, or using a selective oligomerization unit such as that described above in the first implementation upstream of the oligomerization unit. The oligomers produced then have fewer branches than those obtained by treating the complete cut including isobutene.

Third Implementation

A third implementation of the process of the invention consists of subjecting an olefinic C4 cut optionally containing traces of propylene to oligomerization such that the major portion of the butenes contained in the feed is converted into dimers or trimers which are then used as gasoline stock. In said third implementation of the process of the invention, at least 90% by weight of the 1-butenes, at least 80% by weight of the 2-butenes, at least 97% by weight of the isobutene and at least 80% by weight of the propylene are converted. Said third implementation of the process of the invention can produce a maximum quantity of gasoline without producing kerosene. The olefinic C4 cut usually comprises isobutane, n-butane, 1-butene, 2-butene, isobutene and possibly a small quantity of butadiene. The butadiene is generally eliminated upstream of the oligomerization step by a selective hydrogenation step to avoid polymerization reactions which would render the catalyst inactive.

Said process which is carried out in accordance with said third implementation comprises the following steps:
 a first oligomerization step: an olefinic C4 cut is treated in a first oligomerization reactor in which the overall conversion of n-butenes in the feed is less than 45% by weight and the isobutene conversion is more than 80% by weight, preferably more than 85% by weight, the oligomers obtained being more than 80% by weight dimers and trimers;
 the effluent from the first oligomerization step is sent to a fractionation column to recover a first fraction containing isobutene and unconverted n-butenes and a second fraction consisting of 90% by weight dimers and trimers from the oligomerization reaction;

a second oligomerization step: said first recovered fraction is introduced into a second oligomerization reactor in which most of the olefins are converted into dimers and trimers, i.e. at least 50% by weight of n-butenes are converted; preferably, at least 75% by weight of the 1-butene and at least 55% by weight of the 2-butenes are converted; and the effluent from the second oligomerization step is sent to the fractionation column associated with the first oligomerization reactor or to a second column to separate the gasoline or kerosene from the unconverted C4 compounds.

In the oligomerization reactors, the temperature is between 40° C. and 250° C., preferably between 45° C. and 200° C., and the pressure is between 0.1 and 10 MPa, preferably between 0.1 and 6 MPa, and the quantity of hydrocarbon feed per volume of catalyst per hour is between 0.05 and 5 $h^{-1}$, preferably between 0.1 and 2.5 $h^{-1}$. The reactor technology may be that of a fixed bed, fluidized bed or moving bed reactor. Preferably, it is a fixed bed reactor.

Preferably, in the second oligomerization reactor, the operating conditions are more severe than in the first reactor.

Said third implementation of the process of the invention may be applied to a $C_3$-$C_4$ olefinic feed.

Fourth Implementation

In accordance with said fourth implementation, an olefinic C4 cut or an olefinic C3-C4 cut is brought into contact with the oligomerization catalyst as described in the present description such that the major portion of the butenes contained in the feed are converted, to form gasoline stock and a kerosene base. In this fourth implementation of the process of the invention, at least 90% by weight of the 1-butene, at least 80% by weight of the 2-butenes and at least 97% by weight of the isobutene are converted. The olefinic C4 cut normally essentially comprises isobutane, n-butane, 1-butene, 2-butene, isobutene and possibly a small quantity of butadiene. The olefinic C3-C4 cut also contains propane and propylene in the proportions given hereinabove.

In the oligomerization reactor, the temperature is between 60° C. and 250° C., preferably between 100° C. and 200° C., and the pressure is between 0.1 and 10 MPa, preferably between 0.1 and 6 MPa, and the quantity of hydrocarbon feed per volume of catalyst per hour is between 0.05 and 5 $h^{-1}$, preferably between 1 and 2.5 $h^{-1}$. The reactor technology may be that of a fixed bed, fluidized bed or moving bed reactor. Preferably, it is a fixed bed reactor.

Fifth Implementation

In said fifth implementation, an olefinic C3 cut is brought into contact with said oligomerization catalyst described in the present description such that the major portion of the propylene contained in the feed is converted, i.e. at least 80% by weight of the propylene contained in the feed is converted to form gasoline stock and a kerosene base. The olefinic C3 cut normally comprises at least 90% by weight propylene and propane.

The oligomerization reaction is carried out at a temperature between 30° C. and 300° C., the pressure is between about 0.1 and 20 MPa, and the quantity of hydrocarbon feed per volume of catalyst per hour is between 0.05 and 5 $h^{-1}$. Preferably, the temperature is between 40° C. and 160° C., the pressure is between 2 and 7 MPa and the volume of hydrocarbon feed sent per volume of catalyst per hour is preferably between 0.1 and 2.5 $h^{-1}$. The reactor technology may be that of a fixed bed, fluidized bed or moving bed reactor. Preferably, it is a fixed bed reactor.

Characterization Techniques

The catalyst based on a silica-alumina used in the oligomerization process of the invention is characterized using several analysis techniques, in particular by wide angle X-ray diffraction (WAXD), by nitrogen adsorption isotherm, by mercury intrusion porosimetry, by transmission electron microscopy (TEM), optionally coupled with energy selection X-ray spectrometric analysis (EXD), by solid aluminium atom nuclear magnetic radiation ($^{27}$Al MAS NMR), by infrared spectroscopy (IR) and by X-ray fluorescence (XF) or atomic absorption (AA). The density of the catalyst used in the process of the invention is also evaluated.

The wide angle X-ray diffraction technique (values of the angle 2θ in the range 5° to 70°) can characterize a crystalline solid defined by repetition of a unit motif or unit cell on the molecular scale. In the discussion below, powder X-ray analysis is carried out with a diffractometer operating in reflection and provided with a back monochromator using the radiation line of copper (wavelength 1.5406 Å). The peaks which are normally observed on diffractograms corresponding to a given value of the angle 2θ are associated with the interplanar spacings $d_{(hkl)}$ which are characteristic of the structural symmetry (ies) of the catalyst, ((hkl) being the Miller indices of the reciprocal lattice) by the Bragg relationship: $2d_{(hkl)} \times \sin(\theta) = n \times \lambda$. This indexation can then allow the lattice parameters (abc) of the direct lattice to be determined. In particular, the two most intense peaks are located at a position corresponding to a "d" in the range 1.39 to 1.40 Å and a "d" in the range 1.97 to 2.00 Å. The term "gamma alumina" as used in the remainder of the text means, inter alia and as an example, an alumina included in the group composed of cubic gamma, pseudo-cubic gamma, tetragonal gamma, low or poor crystallinity gamma, large surface area gamma, low surface area gamma, gamma from coarse boehmite, gamma from crystalline boehmite, gamma from low or poor crystallinity boehmite, gamma from a mixture of crystallized boehmite and an amorphous gel, gamma from an amorphous gel, gamma moving towards delta. For the positions of the diffraction peaks of eta, delta and theta aluminas, reference should be made to the article by B C Lippens, J J Steggerda in "Physical and Chemical Aspects of Adsorbents and Catalysts", E G Linsen (Ed), Academic Press, London, 1970, 171. For the catalyst used in the process of the invention, the X-ray diffraction diagram shows a broad peak which is characteristic of the presence of amorphous silica. Further, in the following text, the alumina compound may contain an amorphous fraction which is difficult to detect by XRD techniques. It will thus be understood below that the alumina compounds used or described in the text may contain an amorphous or poorly crystalline fraction.

Nitrogen adsorption isotherm analysis corresponding to physical adsorption of molecules of nitrogen in the pores of the catalyst via a progressive increase in the pressure at constant temperature provides information regarding the particular textural characteristics (pore diameter, pore type, specific surface area) of the oligomerization catalyst used in the process of the invention. In particular, it can provide access to the specific surface area and to the mesopore distribution of said catalyst. The term "specific surface area" means the BET specific surface area ($S_{BET}$ in $m^2/g$) determined by nitrogen adsorption in accordance with ASTM "D" 3663-78 established using the BRUNAUER-EMMETT-TELLER method described in the periodical "The Journal of the American Society" 1938, 60, 309. The pore distribution representative of a population of mesopores centred in a range of 1.5 to 50 nm is determined by the Barrett-Joyner-Halenda model (BJH). The nitrogen adsorption-desorption isotherm using the BJH model is described in the periodical "The Journal of the American Society" 1951, 73, 373 by E P Barrett, L G Joyner and P P Halenda. In the description below, the term "nitrogen adsorption volume of the catalyst" corresponds to the volume measured for $P/P_0=0.99$, the pressure at which it is assumed that nitrogen has filled all of the pores. Finally, the term "surface adsorption" means the surface area measured on the adsorption isotherm branch. Reference should be made, for example, to the article by A Lecloux in "Mémoires de la Société Royale des Sciences de Liège", $6^{th}$ series, 1971, volume 1, section 4, pp 169.

In the description below, the "mercury volume of the catalyst" corresponds to the volume measured by mercury porosimetry intrusion in accordance with American standard ASTM D4284-83 at a maximum pressure of 4000 bar, using a surface tension of 484 dyne/cm and a contact angle for the oligomerization catalyst comprising an amorphous silica-alumina of 140°. The mean mercury diameter is defined as being a diameter such that all pores with a size smaller than that diameter constitute 50% of the pore volume ($V_{Hg}$), in a range of 36 Å to 1000 Å. The wetting angle was taken to be 1400 in accordance with the recommendations in the work "Techniques de l'ingénieur, traité analyse et caracterisation" [Engineering techniques: analysis and characterization], 1050, by J Charpin and B Rasneur. In order to provide better precision, the value of the total mercury volume in ml/g given in the text below corresponds to the value of the total mercury volume in ml/g measured on the sample less than value of the mercury volume in ml/g measured on the same sample for a pressure corresponding to 30 psi (approximately 2 bar). In order to better characterize the pore distribution resulting from mercury intrusion analysis, the following pore distribution criteria are defined: the volume V2 corresponds to the volume contained in pores with a diameter equal to or greater than the mean diameter minus 30 Å and less than or equal to the mean diameter plus 30 Å and the volume V3 corresponds to the volume contained in pores with a diameter equal to or more than the mean diameter plus 30 Å.

Transmission electron microscopy (TEM) is also a technique which is widely used to characterize the oligomerization catalyst based on silica-alumina used in the process of the invention. This allows an image of the solid being studied to be formed, the contrasts observed being characteristic of the structural organization, the texture, the morphology or the composition of the particles observed, the maximum resolution of the technique being 0.2 nm. To this end, an electron microscope (of the Jeol 2010 or Philips Tecnai20F type, with optional scanning) is used, provided with an energy selection X-ray spectrometer (EXD) (for example a Tracor or Edax). The EXD detector has to allow detection of light elements. The combination of the two tools, TEM and EXD, could combine imagery and local chemical analysis with good spatial resolution. For this type of analysis, dry samples are finely ground in a mortar; the powder is then included in resin to produce ultrafine sections with a thickness of about 70 nm. Such sections are collected on copper grids coated with a film of perforated amorphous carbon acting as a support. They are then introduced into the microscope for observation and analysis under high vacuum. When imaged, the sample zones are readily distinguished from the resin zones. A certain number of analyses are then carried out, a minimum of 10, preferably in the range 15 to 30, on different zones of the sample. The size of the electron beam for zone analysis (approximately determining the size of the analyzed zones) is 50 nm in diameter as a maximum, preferably 20 nm, and more preferably 10, 5, 2 or 1 nm in diameter. In scanning mode, the analyzed zone will be a function of the size of the scanned zone and not the size of the beam, which is generally less. Semi-quantitative processing of X-ray spectra recorded using the EXD spectrometer can produce the relative concentration of Al and Si (as an atomic %) and the Si/Al ratio for each of the analyzed zones. The mean $Si/Al_m$ and the standard deviation a of this set of measurements can then be calculated. In the non-limiting examples of the description which follows, the 50 nm probe was used to characterize the oligomerization catalyst based on silica-alumina used in the process of the invention unless otherwise indicated.

The oligomerization catalyst comprising a silica-alumina and used in the process of the invention was analyzed by solid $^{27}$Al MAS NMR using a Brüker MSL 400 type spectrometer with a 4 mm probe. The sample rotation rate was of the order of 11 kHz. Aluminium NMR can potentially distinguish between three types of aluminium which have the following chemical displacements:

between 100 and 40 ppm, tetra-coordinated type aluminium, $Al_{IV}$;
between 40 and 20 ppm, penta-coordinated type aluminium, $Al_V$;
between 20 and −100 ppm, hexa-coordinated type aluminium, $Al_{VI}$;

The aluminium atom is a quadripolar nucleus. Under certain analytical conditions (weak radiofrequency field: 30 kHz, low pulse angle: $\pi/2$ and water-saturated sample), the magic angle spinning (MAS) NMR technique is a quantitative technique. The decomposition of MAS NMR spectra allows direct access to the quantity of the various species. The spectrum is calibrated as the chemical displacement with respect to a 1 M aluminium nitrate solution. The aluminium signal is at zero ppm. It was elected to integrate the signals between 100 and 20 ppm for $Al_{VI}$ and $Al_V$, which corresponds to area 1, and between 20 and −100 for $Al_{VI}$ which corresponds to area 2. In the following description of the invention, the term "proportion of octahedral $Al_{VI}$" means the following ratio: area 2/(area 1+area 2).

The acidity of the oligomerization catalyst is measured by infrared spectroscopy. The IR spectra were recorded on a Nicolet Nexus-670 type interferometer at a resolution of 4 $cm^{-1}$ with Happ-Gensel type apodisation. The sample (20 mg) was pressed into a self-supporting pellet and placed in an in situ analytical cell (25° C. to 550° C., furnace offset from IR beam, high vacuum of $10^{-6}$ mbars). The pellet diameter was 16 mm. The sample was pre-treated as follows to eliminate physisorbed water and to partially dehydroxylate the catalyst surface to provide an image which was representative of the catalyst acidity when in operation:

temperature ramp-up from 25° C. to 300° C. over 3 hours;
constant temperature stage for 10 hours at 300° C.;
temperature ramp-down from 300° C. to 25° C. over 3 hours.

The basic probe (pyridine) was then adsorbed at saturating pressure at 25° C. then thermo-desorbed in the following constant temperature stages:

25° C. for 2 hours under high vacuum;
100° C. for 1 hour under high vacuum;
200° C. for 1 hour under high vacuum;
300° C. for 1 hour under high vacuum.

A spectrum was recorded at 25° C. at the end of the pre-treatment and at each desorption stage in transmission mode with an accumulation time of 100 s. The spectra were recorded at iso-mass (and thus assumed to be iso-thickness) (exactly 20 mg). The number of Lewis acid sites is proportional to the surface area of the peak with a maximum near 1450 $cm^{-1}$ including shoulders. The number of Bronsted acid sites is proportional to the surface area of the peak with a maximum near 1545 cm$^{-1}$. The ratio of the number of Bronsted acid sites/number of Lewis acid sites, B/L, is estimated to be equal to the ratio of the surface areas of the two peaks described above. In general, the surface areas of the peaks at 25° C. are used. This ratio B/L is generally calculated from the spectrum recorded at 25° C. after adsorption of the pyridine and the constant temperature stage of 2 h in a high vacuum.

The overall composition of the oligomerization catalyst used in the process of the invention, in particular the quantity of the element sodium, may be determined by X-ray fluorescence (XF) on said catalyst in the powdered state or by atomic absorption (AA) after acid attack of said catalyst.

The settled packing density (SPD) is measured as described in "Applied Heterogeneous Catalysis" by J F Le Page, J Cosyns, P Courty, E Freund, J-P Franck, Y Jacquin, B Juguin, C Marcilly, G Martino, J Miquel, R Montamal, A Sugier, H Van Landeghem, Technip, Paris, 1987, chapter 6.2.4, pages 167-168. A suitably sized graduated cylinder is filled by successive additions and, between two successive additions, the catalyst is settled by shaking the cylinder to constant volume. This measurement is generally carried out on 1000 cm$^3$ of catalyst packed into a cylinder with a height-to-diameter ratio of close to 5:1. This measurement is preferably carried out using automated apparatus such as the Autotap® sold by Quantachrome®.

The following examples illustrate the present invention without in any way limiting its scope.

EXAMPLE 1

Preparation and Shaping of a Catalyst Constituted by a Silica-alumina SA1 (in Accordance with the Invention)

The catalyst constituted by silica-alumina SA1 of the invention was prepared by initially mixing a combination formed by an alumina compound and a silica compound, each being completely soluble in said mixture (the ratio R described above in the present description being 0.92) with an alumina compound which is partially soluble in an acid medium. To prepare said combination, the following is carried out: firstly, a 30% sulphuric acid solution was added to a solution of sodium silicate. The quantity of H$_2$SO$_4$ was defined so as to operate with a fixed degree of neutralization. Addition was carried out over two minutes with agitation at 600 rpm. The synthesis temperature was 60° C. The maturation period was fixed at 30 minutes. Agitation was maintained at 600 rpm, the temperature was than of the preceding step. Next, Al$_2$(SO$_4$)$_3$ (500 ml) was added; the concentration was fixed by the desired alumina content. The pH was not regulated and it was fixed by the desired alumina content. Addition was carried out over 10 minutes. Agitation was still fixed at 600 rpm, the temperature was the same as that of the preceding steps. Next, ammonia was added. The gel obtained was filtered by displacement. Washing was carried out with water at 60° C., 3 kg of water per kg of solid contained in the gel. Next, an exchange with ammonium nitrate NH$_4$NO$_3$ (138.5 g/l) at 60° C. and 1.5 l per kg of solid contained in the gel was carried out. Finally, additional washing with water at 60° C. was carried out by displacement, 3 kg of water per kg of solid contained in the gel. The gel from this step was mixed with Pural boehmite powder (partially soluble alumina compound) such that the final composition in the mixed solid of anhydrous product was, at this stage of the synthesis, 50% of Al$_2$O$_3$-50% SiO$_2$. Mixing was carried out in a Z arm mixer. Extrusion was carried out by passing the paste through a die provided with orifices with a diameter of 1.4 mm. The extrudates obtained were dried at 150° C., calcined at 550° C. then calcined at 700° C. in the presence of 400 g of water per kg of dry air for a period of 6 hours. The characteristics of the catalyst constituted by silica-alumina were as follows:
  the composition of the support was 49% Al$_2$O$_3$ and 51% SiO$_2$;
  the BET surface area was 284 m$^2$/g;
  the total pore volume, measured by mercury intrusion porosimetry, was 0.85 ml/g;
  the mean pore diameter, measured by mercury intrusion porosimetry, was 110 Å;
  the ratio between the volume V2, measured by mercury intrusion porosimetry, between D$_{mean}$−30 Å and D$_{mean}$+30 Å to the total mercury volume was 0.85;
  the volume V3, measured by mercury intrusion porosimetry, included in pores with diameters of more than D$_{mean}$+30 Å was 0.05 ml/g;
  the ratio between the adsorption surface area and the BET surface area was 0.76;
  the pore volume, measured by mercury intrusion porosimetry, included in pores with diameters of more than 160 Å was 0.04 ml/g;
  the pore volume, measured by mercury intrusion porosimetry, included in pores with diameters of more than 200 Å was 0.03 ml/g;
  the pore volume, measured by mercury intrusion porosimetry, included in pores with diameters of more than 500 Å was 0.009 ml/g;
  the settled packing density of the support was 0.47 g/cm$^3$;
  the X-ray diffraction diagram contained the principal characteristic peaks of gamma alumina and in particular contained peaks with a "d" in the range 1.39 to 1.40 Å and a "d" in the range 1.97 Å to 2.00 Å;
  the B/L ratio for the catalyst was 1;
  the atomic sodium content was 300±20 ppm. The atomic sulphur content was 2500 ppm;
  the solid $^{27}$Al MAS NMR spectrum of the catalysts showed two distinct peak complexes. A first type of aluminium for which the maximum resonates at about 10 ppm extends between −100 and 20 ppm. The position of the maximum suggested that these species were essentially of the Al$_{VI}$ type (octahedral). A second major type of aluminium with a maximum resonating at about 60 ppm extends between 20 and 100 ppm. The predominant species here corresponded to Al$_{IV}$ atoms (tetrahedral);
  the catalyst contained a single silica-alumina zone with a Si/Al ratio, determined by TEM microprobe, of 1.1.

EXAMPLE 2

Preparation and Shaping of a Catalyst Constituted by a Silica-alumina SA2 (Not in Accordance with the Invention)

The aluminium hydroxide powder was prepared using the process described in patent application WO-00/01617. The mean particle size for the aluminium hydroxide particles, measured by laser granulometry, was 40 microns. This powder was mixed with a silica sol prepared by exchange on a decationizing resin, then filtered through a resin with a porosity of 2. The concentrations of silica sol and aluminium hydroxide powder were adjusted to obtain a final composition of 70% Al$_2$O$_3$ and 30% SiO$_2$. Shaping was carried out in the presence of 15% nitric acid with respect to the anhydrous product. Mixing was carried out using a Z arm mixer. Extrusion was carried out by passing the paste through a die provided with 1.4 mm diameter orifices. The extrudates obtained were dried at 150° C. then calcined at 550° C.

The catalyst had the following characteristics:
the silica-alumina catalyst composition was 85.3% $Al_2O_3$ and 14.7% $SiO_2$;
the BET surface area was 430 $m^2/g$;
the total pore volume, measured by nitrogen adsorption, was 0.24 ml/g;
the mean pore diameter, measured by mercury porosimetry, was 46 Å;
the ratio between the volume V2 measured by mercury porosimetry between $D_{mean}$−30 Å and $D_{mean}$+30 Å to the total mercury volume was 0.7;
the volume V3, measured by mercury porosimetry, in pores with diameters of more than $D_{mean}$+30 Å was 0.07 ml/g;
the pore volume, measured by mercury porosimetry, in pores with diameters of more than 160 Å was 0.051 ml/g;
the pore volume, measured by mercury porosimetry, in pores with diameters of more than 200 Å was 0.047 ml/g;
the pore volume, measured by mercury porosimetry, in pores with diameters of more than 500 Å was 0.03 ml/g;
the B/L ratio for the catalyst was 1.1;
the settled packing density of the catalyst was 0.80 $g/cm^3$;
the X-ray diffraction diagram contained the principal characteristic peaks of gamma alumina; in particular, it contained peaks with a "d" in the range 1.39 Å to 1.40 Å and with "d" in the range 1.97 Å to 2.00 Å;
the atomic sodium content was 40±20 ppm. The atomic sulphur content was 200 ppm.
solid $^{27}Al$ MAS NMR spectra of the catalysts showed two distinct peak complexes. A first type of aluminium for which the maximum resonates at about 10 ppm extends between −100 and 20 ppm. The position of the maximum suggested that these species were essentially of the $Al_{VI}$ type (octahedral). A second minor type of aluminium with a maximum resonating at about 60 ppm extends between 20 and 100 ppm. This complex could be resolved into at least two species. The predominant species here corresponded to $Al_{IV}$ atoms (tetrahedral);
the catalyst contained two silica-alumina zones, said zones having Si/Al ratios which are higher or lower than the overall Si/Al ratio determined by X-ray fluorescence. One of the zones had a Si/Al ratio, determined by TEM, of 4.35 and the other zone had a Si/Al ratio, determined by TEM, of 1.75.

EXAMPLE 3

Preparation and Shaping of a Catalyst Constituted by a Silica-alumina SA3 (Not in Accordance with the Invention)

The catalyst constituted by silica-alumina SA3 (not in accordance with the invention) was prepared by initially mixing a combination formed by an alumina compound and a silica compound, each being completely soluble in said mixture, with an alumina compound which is partially soluble in an acid medium. To prepare said combination, the following was carried out: firstly, a 30% sulphuric acid solution was added to a solution of sodium silicate. The quantity of $H_2SO_4$ was defined so as to operate with a fixed degree of neutralization. Addition was carried out over two minutes with agitation at 600 rpm. The synthesis temperature was 60° C. The maturation period was fixed at 30 minutes. Agitation was maintained at 600 rpm, the temperature was that of the preceding step. Next, $Al_2(SO_4)_3$ (500 ml) was added; the concentration was fixed by the desired alumina content. The pH was not regulated and it was fixed by the desired alumina content. Addition was carried out over 10 minutes. Agitation was still fixed at 600 rpm, the temperature was the same as that of the preceding steps. Next, ammonia was added. The gel obtained was filtered by displacement. Washing was carried out with water at 60° C., 3 kg of water per kg of solid contained in the gel. Next, an exchange with ammonium nitrate $NH_4NO_3$ (138.5 g/l) at 60° C. and 1.5 l per kg of solid contained in the gel was carried out. Finally, additional washing with water at 60° C. was carried out by displacement, 3 kg of water per kg of solid contained in the gel. The gel from this step was mixed with Pural boehmite powder (partially soluble alumina compound) such that the final composition in the mixed solid of anhydrous product was, at this stage of the synthesis, 50% of $Al_2O_3$-50% $SiO_2$. Mixing was carried out in a Z arm mixer. Extrusion was carried out by passing the paste through a die provided with orifices with a diameter of 1.4 mm. The extrudates obtained were dried at 150° C., calcined at 550° C. then calcined at 700° C. in the presence of 400 g of water per kg of dry air for a period of 2 hours.

The characteristics of the catalyst constituted by silica-alumina were as follows:
the composition of the support was 49% $Al_2O_3$ and 51% $SiO_2$;
the BET surface area was 270 $m^2/g$;
the total pore volume, measured by mercury intrusion porosimetry, was 0.55 ml/g;
the mean pore diameter, measured by mercury intrusion porosimetry, was 7.5 Å;
the ratio between the volume V2, measured by mercury intrusion porosimetry, between $D_{mean}$−30 Å and $D_{mean}$+30 Å to the total mercury volume was 0.85;
the volume V3, measured by mercury intrusion porosimetry, included in pores with diameters of more than $D_{mean}$+30 Å was 0.07 ml/g;
the ratio between the adsorption surface area and the BET surface area was 0.75;
the pore volume, measured by mercury intrusion porosimetry, included in pores with diameters of more than 160 Å was 0.04 ml/g;
the pore volume, measured by mercury intrusion porosimetry, included in pores with diameters of more than 200 Å was 0.03 ml/g;
the pore volume, measured by mercury intrusion porosimetry, included in pores with diameters of more than 500 Å was 0.009 ml/g;
the settled packing density of the support was 0.63 $g/cm^3$;
the X-ray diffraction diagram contained the principal characteristic peaks of gamma alumina and in particular contained the peaks with a "d" in the range 1.39 to 1.40 Å and a "d" in the range 1.97 Å to 2.00 Å;
the B/L ratio for the catalyst was 1;
the atomic sodium content was 300±20 ppm. The atomic sulphur content was 2500 ppm;
the solid $^{27}Al$ MAS NMR spectra of the catalysts showed two distinct peak complexes. A first type of aluminium for which the maximum resonates at about 10 ppm extends between −100 and 20 ppm. The position of the maximum suggested that these species were essentially of the $Al_{VI}$ type (octahedral). A second major type of aluminium with a maximum resonating at about 60 ppm extends between 20 and 100 ppm. The predominant species here corresponded to $Al_{IV}$ atoms (tetrahedral);
the support contained a single silica-alumina zone with a Si/Al ratio, determined by TEM microprobe, of 1.1.

EXAMPLE 4

Catalytic evaluation of Silica-aluminas SA1, SA2 and SA3 in a High Conversion Oligomerization Process (Second Implementation)

An olefinic C4 cut from a steam cracking unit underwent a selective hydrogenation treatment to eliminate butadiene, then was dried over a type 13X molecular sieve to eliminate traces of sulphur and water.

The composition of the feed after said treatments was as follows:

| Composition of feed (weight %) | |
|---|---|
| Isobutane | 1.55 |
| n-butane | 7.74 |
| Isobutene | 39.89 |
| 1-butene | 28.64 |
| Σ 2-butenes | 22.18 |

This feed was sent to an isothermal oligomerization reactor containing the silica-alumina based catalyst SA1, SA2 or SA3. The operating conditions were as follows:

| | Catalyst | | |
|---|---|---|---|
| | SA1 in accordance | SA2 not in accordance | SA3 not in accordance |
| Pressure | 6.0 MPa | 6.0 MPa | 6.0 MPa |
| Temperature | 130° C. | 130° C. | 130° C. |
| HSV | 2 h$^{-1}$ | 2 h$^{-1}$ | 2 h$^{-1}$ |

At the outlet from the oligomerization reactor, the composition by weight of the effluent was as follows:

| Composition of effluent (weight %) | Catalyst | | |
|---|---|---|---|
| | SA1 In accordance | SA2 Not in accordance | SA3 Not in accordance |
| Isobutane | 3.58 | 3.64 | 3.43 |
| n-butane | 8.01 | 7.89 | 7.82 |
| Isobutene | — | — | — |
| 1-butene | 0.23 | 0.26 | 0.26 |
| Σ 2-butenes | 5.77 | 6.81 | 6.80 |
| C5+ polymer | 82.41 | 81.40 | 81.69 |

The use of catalyst SA1 resulted in a yield of C5+ polymer that was higher than with catalysts SA2 and SA3. Said C5+ fraction could be used as gasoline stock. Catalyst SA1 was thus more selective than catalysts SA2 and SA3.

EXAMPLE 5

Catalytic Evaluation of Silica-aluminas SA1, SA2 and SA3 in a Moderate Conversion Oligomerization Process (First Implementation)

An olefinic C4 cut from a steam cracking unit underwent a selective hydrogenation treatment to eliminate butadiene, then was dried over a type 13X molecular sieve to eliminate traces of sulphur and water. The composition of the feed after said treatments was as follows:

| Composition of feed (weight %) | |
|---|---|
| Isobutane | 1.50 |
| n-butane | 6.63 |
| Isobutene | 49.48 |
| 1-butene | 27.86 |
| Σ 2-butenes | 14.53 |

This feed was sent to an isothermal oligomerization reactor containing the catalyst based on silica-alumina SA1, SA2 or SA3. The operating conditions were as follows:

| Catalyst | SA1 | SA2 | SA3 |
|---|---|---|---|
| Pressure | 2.0 MPa | 2.0 MPa | 2.0 MPa |
| Temperature | 80° C. | 80° C. | 80° C. |
| HSV | 0.5 h$^{-1}$ | 0.5 h$^{-1}$ | 0.5 h$^{-1}$ |

At the outlet from the oligomerization reactor, the composition by weight of the effluent was as follows:

| Composition of effluent (weight %) | Catalyst | | |
|---|---|---|---|
| | SA1 | SA2 | SA3 |
| Isobutane | 1.58 | 1.57 | 1.58 |
| n-butane | 6.69 | 6.64 | 6.68 |
| Isobutene | 0.37 | 0.41 | 0.40 |
| 1-butene | 20.10 | 22.90 | 22.61 |
| Σ 2-butenes | 21.36 | 19.01 | 19.24 |
| C5+ polymer | 49.90 | 49.47 | 49.49 |

The use of catalyst SA1 resulted in a yield of C5+ polymer that was higher than with catalysts SA2 and SA3. Said C5+ fraction could be used as gasoline stock. Thus, catalyst SA1 was more selective than catalysts SA2 and SA3.

EXAMPLE 6

Catalytic Evaluation of Catalysts Based on Silica-aluminas SA1, SA2 and SA3 in a High Conversion Oligomerization Process (Second Implementation)

An olefinic C4 cut from a catalytic cracking unit underwent a selective hydrogenation treatment to eliminate butadiene, then was dried over a type 13X molecular sieve to eliminate traces of sulphur and water.

The composition of the feed after said treatments was as follows:

| Composition of feed (weight %) | |
|---|---|
| Isobutane | 29.10 |
| n-butane | 11.45 |
| Isobutene | 14.22 |
| 1-butene | 14.20 |
| Σ 2-butenes | 31.03 |

This feed was sent to an isothermal oligomerization reactor containing the silica-alumina based catalyst SA1, SA2 or SA3. The operating conditions were as follows:

| Catalyst | SA1 | SA2 | SA3 |
|---|---|---|---|
| Pressure | 6.0 MPa | 6.0 MPa | 6.0 MPa |
| Temperature | 125° C. | 125° C. | 125° C. |
| HSV | 2 h$^{-1}$ | 2 h$^{-1}$ | 2 h$^{-1}$ |

At the outlet from the oligomerization reactor, the composition by weight of the effluent was as follows:

| Composition of effluent | Catalyst | | |
|---|---|---|---|
| (weight %) | SA1 | SA2 | SA3 |
| Isobutane | 29.38 | 29.42 | 29.30 |
| n-butane | 11.43 | 11.45 | 11.45 |
| Isobutene | 0.08 | 0.08 | 0.31 |
| 1-butene | 1.92 | 2.41 | 4.03 |
| Σ 2-butenes | 22.34 | 23.15 | 36.25 |
| C5+ polymer | 34.85 | 33.49 | 18.66 |

The use of catalyst SA1 resulted in a yield of C5+ polymer that was higher than with catalysts SA2 and SA3. Said C5+ fraction could be used as gasoline stock. Catalyst SAT was thus more selective than catalysts SA2 and SA3.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. No. 08/00.437, filed Jan. 28, 2008, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for oligomerizing an olefinic hydrocarbon feed, comprising bringing said feed into contact with a catalyst comprising a silica-alumina, the silica content of said catalyst being in the range 5% to 95% by weight, said catalyst being prepared by a process comprising at least:
   a) mixing at least one alumina compound which is partially soluble in an acid medium with either at least one silica compound which is completely soluble in the reaction mixture or a combination formed by at least one silica compound and at least one alumina compound, said silica and alumina compounds being completely soluble in the reaction mixture, in order to form a solid precursor of said catalyst;
   b) hydrothermal treatment of the solid precursor resulting from step a) by calcining in moist air for a period in the range of 4 to 7 hours, in the presence of steam having more than 20 g water per kg of dry air.

2. A process according to claim 1, in which said catalyst is wholly constituted by said silica-alumina.

3. A process according to claim 1, in which said alumina compound which is partially soluble in an acid medium is of the formula $Al_2O_3, nH_2O$ ($n \leq 5$) and has a specific surface area in the range of 150 to 600 m$^2$/g.

4. A process according to claim 1 wherein step a), comprises mixing said at least one alumina compound which is partially soluble in an acid medium with at least one silica compound which is completely soluble in the reaction mixture.

5. A process according to claim 4, in which the completely soluble silica compound is provided by a source selected from silicic acid, colloidal silicic acid solutions, hydrosoluble alkaline silicates and cationic silicon salts, Ludox® in ammoniacal form or alkaline form, and quaternary ammonium silicates.

6. A process according to claim 1 wherein said step a), comprises mixing said at least one alumina compound which is partially soluble in an acid medium with a combination formed by at least one silica compound and at least one alumina compound, said silica and alumina compounds being completely soluble in the reaction mixture.

7. A process according to claim 6, comprising providing completely soluble hydrated silica-aluminas as a source of said combination.

8. A process according to claim 1, in which said hydrothermal treatment by calcining in moist air is carried out at a temperature in the range 600° C. to 1100° C.

9. A process according to claim 8, in which said calcining in moist air is carried out in the presence of an amount of steam having more than 20 g of water per kg of dry air.

10. A process according to claim 1, in which said olefinic hydrocarbon feed is an olefinic C3 cut comprising at least 90% by weight of propylene and propane.

11. A process according to claim 1, in which said olefinic hydrocarbon feed is an olefinic C3-C4 cut.

12. A process according to claim 1, in which said olefinic hydrocarbon feed is an olefinic C4 cut comprising more than 90% by weight of isobutane, n-butane, 1-butene, 2-butenes and isobutene.

13. A process according to claim 1, in which said olefinic hydrocarbon feed is an olefinic C5 cut.

14. A process according to claim 3, in which said catalyst is wholly constituted by said silica-alumina.

15. A catalyst comprising a non-zeolitic silica-alumina, the silica content of said catalyst being in the range 5% to 95% by weight, said catalyst being prepared by a process comprising at least:
   a) mixing at least one alumina compound which is partially soluble in an acid medium with either at least one silica compound which is completely soluble in the reaction mixture or a combination formed by at least one silica compound and at least one alumina compound, said silica and alumina compounds being completely soluble in the reaction mixture, in order to form a solid precursor of said catalyst;
   b) hydrothermal treatment of the solid precursor resulting from step a) by calcining in moist air for a period in the range of 4 to 7 hours, in the presence of steam having more than 20 g water per kg of dry air.

16. A catalyst according to claim 15, in which said catalyst is wholly constituted by said silica-alumina.

17. A catalyst according to claim 15, in which said alumina compound which is partially soluble in an acid medium is of the formula $Al_2O_3, nH_2O$ ($n \leq 5$) and has a specific surface area in the range of 150 to 600 m$^2$/g.

18. A catalyst according to claim 15 wherein step a), comprises mixing said at least one alumina compound which is partially soluble in an acid medium with at least one silica compound which is completely soluble in the reaction mixture.

19. A catalyst according to claim 15, in which said hydrothermal treatment by calcining in moist air is carried out at a temperature in the range 600° C. to 1100° C.

20. A catalyst according to claim 15, in which said calcining in moist air is carried out in the presence of an amount of steam having more than 20 g of water per kg of dry air.

21. A catalyst according to claim 16, having a total pore volume in the range of 0.65 to 0.9 ml/g.

22. A catalyst according to claim 16, having a total pore volume in the range of 0.7 to 0.9 ml/g.

23. A catalyst according to claim 15, having the following characteristics:
- a silica content in the range of 25% to 75% by weight;
- a content of total alkali compounds of less than 0.025% by weight;
- a content of anionic impurities of less than 0.1% by weight;
- a mean catalyst pore diameter, denoted $D_{mean}$, measured by mercury intrusion porosimetry, in the range of 50 to 100 Å;
- a ratio between the volume V2, measured by mercury intrusion porosimetry, occupied by pores with a diameter in the range between $D_{mean}$ −30 Å and $D_{mean}$ +30 Å, to the total pore volume, measured by mercury intrusion porosimetry, of more than 0.8;
- a volume V3 occupied by pores with diameters of more than $D_{mean}$ +30 Å, measured by mercury intrusion porosimetry, of less than 0.04 ml/g;
- a total pore volume, measured by mercury intrusion porosimetry, and by nitrogen adsorption isotherm, in the range of 0.7 ml/g to 0.9 ml/g;
- a BET specific surface area in the range of 150 to 250 m$^2$/g,
- an adsorption surface area, defined using the branch of a hysteresis curve for nitrogen adsorption isotherm for pores with a diameter in the range of 3 to 200 nm, being such that the ratio between the adsorption area and the BET surface area is more than 0.8;
- a pore volume, measured by mercury intrusion porosimetry, included in pores with a diameter of more than 160 Å, of less than 0.01 ml/g;
- a pore volume, measured by mercury intrusion porosimetry, included in pores with a diameter of more than 200 Å, of less than 0.01 ml/g;
- a pore volume, measured by mercury intrusion porosimetry, included in pores with a diameter of more than 500 Å, of less than 0.01 ml/g;
- an X-ray diffraction diagram of the oligomerization catalyst contains at least the principal characteristic peaks of at least one of the transition aluminas included in the group composed of alpha, rho, khi, kappa, eta, gamma, theta, and delta aluminas; the diagram contains peaks at a "d" in the range 1.39 to 1.40 Å and at a "d" in the range 1.97 Å to 2.00 Å
- a ratio of the number upon Bronsted acid sites/number of Lewis acid sites, B/L, of 0.05-6; and
- a settled packing density of more than 0.50 g/cm$^3$.

24. A process according to claim 1 wherein hydrothermal treatment in (b) is carried out in the presence of steam having more than 40 g of water per kg of dry air.

25. A process according to claim 1 wherein hydrothermal treatment in (b) is carried out in the presence of steam having more than 100 g of water per kg of dry air.

26. A catalyst according to claim 15 wherein hydrothermal treatment in (b) is carried out in the presence of steam having more than 40 g of water per kg of dry air.

27. A catalyst according to claim 15 wherein hydrothermal treatment in (b) is carried out in the presence of steam having more than 100 g of water per kg of dry air.

* * * * *